(12) United States Patent
Wang et al.

(10) Patent No.: US 7,807,363 B2
(45) Date of Patent: Oct. 5, 2010

(54) SUPEROXIDE DISMUTASE-2 EXPRESSION FOR GLAUCOMA DIAGNOSIS

(75) Inventors: Wan-Heng Wang, Grapevine, TX (US); Loretta Graves McNatt, Hurst, TX (US); Abbot F. Clark, Arlington, TX (US); Peter G. Klimko, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 11/680,416

(22) Filed: Feb. 28, 2007

(65) Prior Publication Data

US 2008/0085878 A1    Apr. 10, 2008

Related U.S. Application Data

(60) Provisional application No. 60/777,603, filed on Feb. 28, 2006.

(51) Int. Cl.
*C12Q 1/68* (2006.01)
*C12P 19/34* (2006.01)
*C12M 1/34* (2006.01)
*G01N 33/53* (2006.01)
*C07H 21/04* (2006.01)

(52) U.S. Cl. .................. 435/6; 435/7.1; 435/91.2; 435/91.51; 435/287.2; 536/23.2; 536/23.5

(58) Field of Classification Search .................. None
See application file for complete search history.

(56) References Cited

U.S. PATENT DOCUMENTS 6,716,581 B2 *  4/2004  Lenz et al. .................. 435/6

| | | |
|---|---|---|
| 2004/0009959 A1 | 1/2004 | Potter et al. |
| 2004/0067519 A1 | 4/2004 | Lenz et al. |
| 2004/0091919 A1 | 5/2004 | Bennett et al. |
| 2005/0202488 A1 | 9/2005 | Brown et al. |

OTHER PUBLICATIONS

Aoyama et al., Nitration of manganese superoxide dismutase in cerebrospinal fluids is a marker for peroxynitrite-mediated oxidative stress in neurodegenerative diseases, Ann Neurol., 2000, vol. 47(4):524-527.

Chung-Man et al., Differential expression of manganese superoxide dismutase and catalase in lung cancer, Cancer Research, 2001, vol. 61(23): 8578-8585.

De Leo et al., Oxidative stress and overexpression of manganese superoxide dismutase in patients with Alzheimer's disease, Neuroscience Letters, 1998, vol. 250(3):173-176.

Friedman et al., SOD2-deficiency anemia: protein oxidation and altered protein expression reveal targets of damage, stress response, and antioxidant responsiveness, Blood, 2004, vol. 104(8): 2565-2573.

(Continued)

*Primary Examiner*—Diana B Johannsen
(74) *Attorney, Agent, or Firm*—Mark E. Flanigan (57) ABSTRACT

The present invention concerns a method for diagnosing or monitoring elevated intraocular pressure or glaucoma in a patient comprising providing a biological sample from the patient and measuring the expression level of a superoxide dismutase-2 (SOD-2) gene in the biological sample. The present invention also concerns methods for treating glaucoma or elevated intraocular pressure in a patient comprising administering to a patient an effective amount of an agent that modulates SOD-2 expression or SOD-2 activity.

8 Claims, 7 Drawing Sheets

QPCR of SOD2 gene expression in normal and glaucoma TM tissues.

OTHER PUBLICATIONS

Hiroi et al., Polymorphisms in the SOD2 and HLA-DRB1 genes are associated with nonfamilial idiopathic dilated cardiomyopathy in Japanese, Biochem Biophys Res Commun,1999, vol. 261(2):332-339.

Kasahara et al., SOD2 protects agains oxidation-induced apoptosis in mouse retinal pigment epithelium: implications for age-related macular degeneration, Invest Opthalmol Vis Science, 2005, vol. 46(9):3426-3434.

Li et al., Phenotypic changes induced in human breast cancer cells by overexpresion of manganese-containing superoxide dismutase, Oncogene, 1995, vol. 10:1989-2000.

Liang et al., Evidence for local production of acute phase response apolipoprotein serum amyloid A in Alzheimer's disease brain, Neuroscience Letters, 1997, vol. 225:73-76.

Lushchak et al., Diethyldithiocarbamate inhibits in vivo Cu,Zn-superoxide dismutase and perturbs free radical processes in the yeast *Saccharomyces cerevisiae* cells, 2005, vol. 338:1739-1744.

Melov et al., Extension of life-span with superoxide dismutase/catalase mimetics, 2000, vol. 289:1567-1569.

O'Hara et al., Acute-phase serum amyloid A production by rheumatoid arthritis synovial tissue, Arthritis Research, 2000, vol. 2:142-144.

Qi et al., SOD2 gene transfer protects against optic neuropathy inducted by deficiency of Complex I, Ann Neurol, 2004, vol. 56:182-191.

Salvemini et al., SOD mimetics are coming of age, Nature Reviews, 2002, vol. 1:367-374.

Tanaka et al., Inducible expression of manganese superoxide dismutase by phorbol 12-myristate 13-acetate is mediated by SP1 in endothelial cells, Arterioscler Thromb Vasc. Biol., 2000, vol. 20:392-401.

Urieli-Shoval et al., Widespread expression of serum amyloid A in histologically normal human tissues:predominant localization to the epithelium, 1998, vol. 46(12):1377-1384.

Wang et al., Increased expression of serum amyloid A in human glaucoma and effecti on IOP, ARVO Abstract 2006; Control Tracking No. 06-A-3606-ARVO.

\* cited by examiner

Fig 1. QPCR of SOD2 gene expression in normal and glaucoma TM tissues.

Fig 2.  QPCR of SOD2 gene expression in normal and glaucoma TM cell lines.

FIGURE 3:
COR = cornea; IRI = iris; CB = ciliary body; TM = trabecular meshwork; LEN = lens; CHO = choroid; RET = retina; ONH = optic nerve head; ON = optic nerve; SCL = sclera Fig 4. QPCR of SOD2 gene expression in SAA (1 μg/ml) treated TM cells.

Fig. 5. ELISA of SOD-2 expression in cultured TM cells (NTM469-05 OS) transduced with Adv.SOD2.

Fig 6. SOD-2 expression in mouse eyes injected with Adv.null ($2 \times 10^7$ pfu/eye, n=2), Adv.SOD2 ($2 \times 10^7$ pfu/eye, n=3) and no injection (n=5). SOD2 was measured by ELISA.

Fig 7. Effect of different titers of Adv.SOD2 on mouse IOP by intravitreal injection. Low titer = $2 \times 10^7$ pfu/eye; high titer = $9 \times 10^7$/eye.

SEQUENCE LISTING

```
<160> NUMBER OF SEQ ID NOS: 3

<210> SEQ ID NO 1
<211> LENGTH: 989
<212> TYPE: DNA
<213> ORGANISM: Homo sapiens

<400> SEQUENCE: 1
tggcttcggc agcggcttca gcagatcggc ggcatcagcg gtagcaccag cactagcagc      60
atgttgagcc gggcagtgtg cggcaccagc aggcagctgg ctccggcttt ggggtatctg     120
ggctccaggc agaagcacag cctccccgac ctgccctacg actacggcgc cctggaacct     180
cacatcaacg cgcagatcat gcagctgcac cacagcaagc accacgcggc ctacgtgaac     240
aacctgaacg tcaacgagga gaagtaccag gaggcgttgg ccaagggaga tgttacagcc     300
cagatagctc ttcagcctgc actgaagttc aatggtggtg gtcatatcaa tcatagcatt     360
ttctggacaa acctcagccc taacggtggt ggagaaccca aagggagtt gctggaagcc      420 atcaaacgtg actttggttc ctttgacaag tttaaggaga agctgacggc tgcatctgtt     480
ggtgtccaag gctcaggttg gggttggctt ggtttcaata aggaacgggg acacttacaa     540
attgctgctt gtccaaatca ggatccactg caaggaacaa caggcctttat tccactgctg    600 gggattgatg tgtgggagca cgcttactac cttcagtata aaaatgtcag gcctgattat     660
ctaaaagcta tttggaatgt aatcaactgg gagaatgtaa ctgaaagata catggcttgc    720
aaaaagtaaa ccacgatcgt tatgctgagt atgttaagct ctttatgact gtttttgtag     780
tggtatagag tactgcagaa tacagtaagc tgctctattg tagcatttct tgatgttgct    840
tagtcactta tttcataaac aacttaatgt tctgaataat ttcttactaa acattttgtt     900
attgggcaag tgattgaaaa tagtaaatgc tttgtgtgat tgaaaaaaaa aaaaaaaaa     960 aaaaaaaaa aaaaaaaaa aaaaaaaa                                        989

<210> SEQ ID NO 2
<211> LENGTH: 222
<212> TYPE: PRT
<213> ORGANISM: Homo sapiens

<400> SEQUENCE: 2
```

-continued

```
Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
                20                  25                  30

Tyr Asp Tyr Gly Ala Leu Glu Pro His Ile Asn Ala Gln Ile Met Gln
            35                  40                  45

Leu His His Ser Lys His His Ala Ala Tyr Val Asn Asn Leu Asn Val
        50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
        130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
            165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
        210                 215                 220
```

<210> SEQ ID NO 3
<211> LENGTH: 25
<212> TYPE: DNA
<213> ORGANISM: Homo sapiens

<400> SEQUENCE: 3
gaacaacagg ccttattcca ctgct                                            25

SUPEROXIDE DISMUTASE-2 EXPRESSION FOR GLAUCOMA DIAGNOSIS

CROSS-REFERENCE TO RELATED APPLICATION

This application claims priority under 35 U.S.C. §119 to U.S. Provisional Patent Application No. 60/777,603, filed Feb. 28, 2006, the entire contents of which are incorporated herein by reference.

TECHNICAL FIELD OF THE INVENTION

The present invention is generally related to improved treatments for glaucoma and elevated intraocular pressure, and more particularly related to glaucoma diagnostics, therapeutics and screening techniques utilizing superoxide dismutase-2 (SOD-2) expression.

BACKGROUND OF THE INVENTION

The eye disease glaucoma is characterized by a permanent loss of visual function due to irreversible damage to the optic nerve. The several morphologically or functionally distinct types of glaucoma are typically characterized by an undesirable elevation of intraocular pressure (IOP), which is considered to be causally related to the pathological course of the disease. Continuously elevated IOP has been associated with the progressive deterioration of the retina and the loss of visual function. In some cases, ocular hypertension, a condition in which IOP is elevated, can present without apparent loss of visual function. However, patients with ocular hypertension are considered to be at a high risk for eventually developing the visual loss associated with glaucoma. Therefore, lowering IOP can be an objective for the treatment of glaucoma patients and for patients with ocular hypertension in order to decrease the potential for, or severity of, glaucomatous retinopathy. Unfortunately, many individuals do not respond well when treated with existing glaucoma therapies.

Glaucoma is currently diagnosed based on specific presenting indications such as optic nerve head changes and visual field loss. However, over half of the patient population with glaucoma are unaware of the disease state, and have already lost approximately 30-50% of retinal ganglion cells by the time of diagnosis. Thus, improved methods for early diagnosis of glaucoma are needed.

Patients known as normotension or low-tension glaucoma patients have relatively low IOP, yet present with glaucomatous visual field loss. These patients may benefit from agents that lower and control IOP, because glaucoma that is detected early and treated promptly may have reduced or reversible loss of visual function. Accordingly, screening techniques are needed that can identify patients at risk for glaucoma, or can detect glaucoma at an early stage before vision loss occurs.

Glaucoma pathology is often associated with changes to the trabecular meshwork. The trabecular meshwork (TM) is a structure associated with aqueous humor (AH) outflow from the eye. Decreases in AH outflow through the TM can cause increases in IOP and potentially result in glaucomatous visual field loss. Identifying potential causes of TM damage may prove to be advantageous for developing glaucoma therapies and/or screening methods.

Certain conventional therapeutic agents are directed at lowering IOP indirectly by, for example, inhibiting AH formation or increasing uveoscleral outflow, and do not address the pathogenic processes involved in glaucoma directly. Furthermore, many of these conventional agents have associated side effects which may render them undesirable as ocular therapeutic agents for lowering IOP or treating glaucoma.

BRIEF SUMMARY OF THE INVENTION

Superoxide dismutase 2 (SOD-2) is a mitochondrial enzyme that converts superoxide to hydrogen peroxide. It acts in oxidative stress responses, and altered SOD-2 activity may contribute to Alzheimer disease, cancer, cardiomyopathy, and other diseases. Embodiments of the present invention recognize in part that expression levels of SOD-2 mRNA may be elevated in glaucomatous trabecular meshwork (TM) tissue. Accordingly, measurement of the levels of SOD-2-associated proteins and genetic material in patient TM tissues and/or other body tissues and/or fluids can help determine whether a patient is at risk of developing glaucoma or elevated intraocular pressure.

In one embodiment, the invention provides a method for diagnosing or monitoring glaucoma in a patient. This method measures, in a biological sample from the patient, the expression level of a gene encoding human SOD-2, where the gene comprises a nucleotide sequence substantially homologous to the sequence of SEQ ID NO:1 set forth below. Expression levels can be measured using various techniques, including direct measurement of SOD-2 mRNA or protein.

In another embodiment, identification of polymorphisms in a subject's SOD-2 genotype may be correlated to an increased risk of that subject developing or presenting with glaucoma.

In another embodiment, the invention provides a method of screening compounds for use as a therapy for glaucoma or elevated intraocular pressure. This method comprises administering a test compound to a mammal and measuring, in a biological sample from the mammal, the level of expression of a gene encoding SOD-2 for the mammal. The level of expression in the biological sample is then compared to the level of SOD-2 expression in a control sample.

In yet another embodiment, modulation of SOD-2 expression is used as a therapeutic modality to treat glaucoma or elevated intraocular pressure.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures. Figures provided herein are intended to help illustrate the invention or assist with developing an understanding of the invention, and are not intended to be definitions of the invention's scope.

BRIEF DESCRIPTION OF THE DRAWING

A more complete understanding of the present invention and the advantages thereof may be acquired by referring to the following description, taken in conjunction with the accompanying drawing and wherein.

DETAILED DESCRIPTION OF THE INVENTION

I. Diagnosis/Risk Assessment

The present invention is concerned in one aspect with the measurement of SOD-2 gene expression levels in a subject to diagnose glaucoma or elevated intraocular pressure. Measuring, as used herein, means to either detect the presence of measured matter, or to quantify or characterize in some aspect such measured matter. Also, it is understood that DNA and RNA sequences, polypeptides, and oligonucleotides specified in certain embodiments of the invention may have slightly different sequences than those identified herein. Such sequence variations are understood by those of ordinary skill in the art to be variations which do not significantly affect the measurement of gene expression in those embodiments.

In one embodiment, a method for diagnosing or monitoring elevated intraocular pressure or glaucoma provides a biological sample from a patient and measures the expression level of a gene in the biological sample. In this embodiment, the gene (hereinafter known as the SOD-2 gene) comprises a nucleotide sequence substantially homologous to the sequence of SEQ ID NO:1.

In other embodiments, a subject's glaucoma risk is determined according to the measured expression level of the SOD-2 gene. In one embodiment, elevated expression of the SOD-2 gene relative to a control level (determined statistically or via normalization using, for example, a housekeeping gene such as 18S RNA) correlates with an increased risk for glaucoma or elevated intraocular pressure.

In yet other embodiments, a subject's glaucoma risk is determined by characterizing the SOD-2 genotype of the subject. Various polymorphic SOD-2 genotypes may produce subject phenotypes with an increased risk of having or developing glaucoma or elevated intraocular pressure. Detection of specific polymorphic markers such as single nucleotide polymorphisms and microsatellite markers, using techniques known to those of skill in the art such as SSCP, PCR, RFLP, etc., may be correlated to a subject's risk of developing and/or having glaucoma. In one embodiment, polymorphisms in a subject's SOD-2 gene are determined by sequencing the subject's SOD-2 gene in a biological sample taken from the subject and comparing the sequence to the sequence set forth in SEQ ID NO:1. Other techniques such as SSCP analysis and protein sequencing could be used instead of nucleic acid sequencing in other embodiments of the present invention.

Known SOD-2 polymorphisms include alanine and valine alleles resulting from amino acid changes at position 16 of the SOD-2 protein (Hiroi et al., *Biochem. Biophys. Res. Comm.* 261:332-339 1999). Polymorphic nucleic acids and proteins generally have sequences substantially homologous to each other, and the sequences set forth in SEQ ID:1 and SEQ ID:2 are intended to also represent such polymorphisms.

Biological samples used with embodiments of the present invention may be tissue or fluid samples from a subject. Various tissues and fluids are usable, such as ocular tissue, aqueous humor, tears, blood, skin, cheek epithelial tissue, and various other tissue and fluid combinations not specifically named herein. In preferred embodiments of the present invention, biological samples are ocular tissues or ocular fluids such as tears or aqueous humor. In certain embodiments, cellular or solid material contained in fluid biological samples is first removed using centrifugation, flow cytometry or other techniques known to those of skill in the art. The separated cellular material is then itself used as a biological sample.

Biological samples may be used directly in embodiments of the invention, or may be processed prior to or during use using techniques disclosed herein or known to those of skill in the art. Processing may include, but is not limited to, isolation of nucleic acids such as DNA, RNA and derivatives thereof, protein isolation, impurity removal, etc. using methods known to those of skill in the art.

A number of different methods can be used in embodiments of the present invention to measure the expression level of the SOD-2 gene. Nucleic acid-based techniques such as nucleotide sequencing, single strand conformational polymorphism (SSCP) analysis, restriction fragment length polymorphism (RFLP) analysis, PCR, RT-qPCR, allele-specific PCR, chip-based analysis, flow cytometry, enzyme-linked immunosorbent assays (ELISA), and other quantitative and qualitative measuring techniques alone or in various combinations can be used to measure expression of the SOD-2 gene in embodiments of the present invention.

In general, embodiments of the invention incorporating techniques such as PCR, nucleotide sequencing, and/or labeled and unlabeled probe detection that rely on nucleic acid hybridization will use oligonucleotides that hybridize to all or a portion of a nucleic acid molecule with a nucleotide sequence substantially homologous to the cDNA sequence set forth in SEQ ID NO:1. Hybridization to nucleotide sequences related to the SEQ ID NO:1 cDNA sequence, such as mRNA or other nucleotides is also contemplated by embodiments of the present invention. Such oligonucleotides may comprise DNA, RNA, cDNA, protein nucleic acid (PNA), genomic DNA, or synthetic oligonucleotides and may be labeled or unlabeled. Oligonucleotide labels can be any of a number of labels known to those of skill in the art, such as digoxigenin, radioisotopes, and fluorescent molecules.

Nucleic acid amplification techniques used in certain embodiments of the present invention generally contact a biological sample with at least one primer consisting essentially of a nucleic acid sequence encoding a consensus sequence of SEQ ID NO:1. Multiple copies of a desired nucleic acid sequence or sequences present in the biological sample are then produced by action of polymerase enzyme together with free nucleotides and cofactors under controlled temperature conditions.

Nucleic acid chip-based methods used in certain embodiments of the present invention generally comprise contacting a biological sample with a solid support-bound nucleic acid molecule that hybridizes under stringent conditions to a nucleotide having a sequence substantially homologous to the sequence of SEQ ID NO:1 and detecting hybridization to measure the expression level of the SOD-2 gene. In preferred embodiments, the solid support is a microarray.

Protein-based methods are used to measure SOD-2 gene expression levels in other embodiments of the present invention. In one embodiment, SOD-2 gene expression is measured by measuring protein levels of a SOD-2 polypeptide substantially homologous to the sequence of SEQ ID NO:2. Measuring such protein levels can be accomplished using methods known to those of skill in the art such as ELISA, capillary electrophoresis, Western blot, immunochromatography, mass spectroscopy, immunohistochemistry, flow cytometry (such as Luminex's XMAP® technology) and protein chip assays.

Protein-based methods used with certain embodiments of the present invention to measure SOD-2 gene expression levels may employ antibodies to expressed SOD-2 protein. Such antibodies may include, but are not limited to, polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Antibodies used may be reactive to protein or nucleic acids, and may be produced using any of a number of antibody production methods known to those of skill in the art.

Other embodiments of the present invention comprise kits for diagnosing or monitoring glaucoma or elevated intraocular pressure. In general, kits comprise a probe set (most often comprising a cDNA, oligonucleotide, or antibody) and reagents for performing a SOD-2 expression measurement assay using expression profiling technology known to those of skill in the art, packaged in a suitable container. The kit may further comprise one or more additional reagents such as substrates, intermediates, labels, primers, tubes and/or other accessories. Such kits may also comprise reagents for collecting blood samples, buffers, extraction reagents, hybridization chambers, etc. Certain embodiments include a software package to perform such functions as data collection and/or analysis, formatting, database accession, security, etc. The kit optionally further comprises an instruction set or user manual detailing preferred methods of using one or more of the kit components for measuring expression levels of SOD-2 gene to diagnose or monitor glaucoma or elevated intraocular pressure.

Such kits may use array-based methods where the probe set is immobilized on an array such as a chip array, a plate array, a bead array, a pin array, a membrane array, a solid surface array, a liquid array, an oligonucleotide array, polynucleotide array or a cDNA array, a microtiter plate, or a membrane and a chip.

II. Screening for Anti-Glaucoma Agents

A further aspect of the present invention provides methods of screening compounds for use as therapies for glaucoma or elevated intraocular pressure. One such embodiment comprises an in-vivo screening method comprising a step of administering a test compound to a mammal. A biological sample is then taken from the mammal and the expression level of a SOD-2 gene is then measured. The measured level of expression is then compared with the level of expression of a control sample, such as a sample taken before administration of the test compound. In preferred embodiments, the SOD-2 gene comprises a nucleotide sequence substantially homologous to the sequence set forth in SEQ ID NO:1. However, the SOD-2 gene measured can be of a sequence specific to the mammal being used, and thus may have a sequence differing from the sequence set forth in SEQ ID:1.

In preferred embodiments of the present invention, altered expression levels of SOD-2 gene in a measured biological sample relative to a control sample are indicative of a desirable compound for use as a therapeutic for glaucoma or elevated intraocular pressure. The measurement of housekeeping gene expression levels (such as 18S RNA) may be used in certain embodiments to normalize measured expression levels of SOD-2 gene. The use of such housekeeping genes for normalization of results is a technique known to those of skill in the art.

As with embodiments of the invention used for diagnosis and/or risk assessment, the expression levels of SOD-2 measured in screening embodiments can be measured using the various nucleic acid and/or protein-based measurement techniques discussed above. Certain embodiments are also provided as a screening kit in a manner similar to the diagnostic kits described above.

In certain embodiments of the present invention, transgenic animals that express modified levels of SOD-2 are used for in vivo screening of compounds. Preferred embodiments use transgenic mice that overexpress murine SOD-2 when compared to wild-type controls. Such mice are available commercially from suppliers such as the Jackson Laboratory (NOD.FVB-Tg(INS—SOD2)). In addition, the SOD-2 gene can be delivered into eyes using a viral transgene expression vector. The effects of altered SOD-2 gene expression can be monitored by measuring IOP.

Other embodiments of the present invention comprise in-vitro methods of screening compounds for use as therapies for glaucoma or elevated intraocular pressure. One such method comprises treating cultured cells with serum amyloid A (SAA) to induce overexpression of SOD-2 by the cells. SAA is an acute-phase reactant whose level in the blood is elevated approximately 1000-fold as part of the body's responses to various injuries, including trauma, infection, inflammation, and neoplasia. As an acute-phase reactant, the liver has been considered to be the primary site of expression. However, extrahepatic SAA expression was described initially in mouse tissues, and later in cells of human atherosclerotic lesions (O'Hara et al. 2000). Subsequently, SAA mRNA was found widely expressed in many histologically normal human tissues. Localized expression was noted in a variety of tissues, including breast, stomach, small and large intestine, prostate, lung, pancreas, kidney, tonsil, thyroid, pituitary, placenta, skin epidermis, and brain neurons. Expression was also observed in lymphocytes, plasma cells, and endothelial cells. SAA protein expression co-localized with SAA mRNA expression has also been reported in histologically normal human extrahepatic tissues (Liang et al. 1997; Urieli-Shoval et al. 1998). SAA levels are elevated in the aqueous humor and TM of glaucoma patients (Wang et al. 2006).

Test compound is administered to the SAA treated cell cultures. The expression level of SOD-2 in the treated cells is then measured by assaying a culture sample of cells. As with biological samples, various preparation methods can be used prior to SOD-2 gene expression measurement. In preferred embodiments, an altered level of expression of SOD-2 gene relative to control samples (statistically-calculated in certain embodiments) is indicative of a desirable compound for the treatment of glaucoma or elevated intraocular pressure.

Another embodiment provides in-vitro methods for screening a compound for glaucoma therapeutic efficacy. In these embodiments, a transgenic cell including a fusion gene is provided. The fusion gene comprises a fragment of SOD-2 gene and a fluorescent reporter. The transgenic cell is then exposed to a test compound. Following exposure, detection of the level of any fluorescent protein produced by the cell determines SOD-2 production and the therapeutic efficacy of the test compound.

Yet another embodiment provides in-vitro methods for screening a compound comprising treating cultured cells with SAA to induce overexpression of SOD-2-regulated genes such as MMP1 and MMP2. A test compound is administered to the SAA-treated cell cultures. The expression level or activities of SOD-2-regulated genes is then measured by assaying a culture sample of cells or supernatant to determine the efficacy of the tested compounds.

Certain embodiments of the present invention provide methods of monitoring the efficacy of a compound in clinical trials for the treatment of glaucoma or elevated intraocular pressure. In these embodiments, a patient sample is assayed for the expression of a polynucleotide having a sequence substantially homologous to the nucleotide sequence of SEQ ID NO:1. The polynucleotide expression level can be assayed using mRNA transcripts of the polynucleotide, probes complementary to the sequence set forth in SEQ ID NO:1, by amplification of cDNA products synthesized from mRNA transcripts, RT-qPCR, by assaying protein products of the nucleotide sequence set forth in SEQ ID NO:1 or a peptide sequence set forth in SEQ ID NO:2, or by other methods known to those of skill in the art. Generally, altered SOD-2 expression levels relative to control values indicate that a compound is efficacious in preferred embodiments.

III. Treatment of Glaucoma

Another aspect of the present invention provides compounds for the treatment of glaucoma and elevated intraocular pressure. Such compounds are identified in certain embodiments according to one or more of the screening methods detailed above. In general, compounds identified according to the screening methods are modulators of SOD-2 expression and/or enzymatic activity.

In certain embodiments, compounds that may be used as SOD-2 modulators are SOD/catalase mimetics such as EUK-8, EUK-134, EUK-189 (*Science*, Vol. 289, no. 5485, pp. 1567-1569, September 2000), and M-40403 (*Nat. Rev. Drug Discov.* 2002, 1(5), 367-374).

In other embodiments, SOD-2 modulators that inhibit SOD-2 expression are used, including, but not limited to protein kinase C (PKC) inhibitors such as calphostin C, tyrosine kinase inhibitors such as genistein (*Arterioscler Thromb Vasc Bio,* 20(2):392-401, February 2000), and other proteins such as FOXO3a, HTATIP, SP1, AFAP1, HSPA1A, IFNG, and VEGF. Inhibitors of SOD-2 enzymatic activity include diethylcarbamodithioic acid (*Biochem. Biophys. Res. Commun.* 2005, 338(4), 1739-1744), 2-methoxyestradiol (also known as 2-ME or Panzem; commercially available from Calbiochem/EMD Biosciences, Inc., 10394 Pacific Center Court, San Diego, Calif., 92121), estrone analog 2-methylthio-3-hydroxy-estra-1,3,5(10)-trien-17-one (U.S. Patent Application Publication No. 2004/0009959, filed Feb. 14, 2003), and 3-amino-1,2,4-triazole (commercially available from Calbiochem/EMD Biosciences, Inc.). The structures of some of the inhibitory SOD-2 modulators are shown below:

diethylcarbamodithioic acid 2-methoxyestradiol

-continued 2-methylthio-3-hydroxy-estra-1,3,5(10)-trien-17-one (I)          3-amino-1,2,4-triazole In yet other embodiments, various agents may be used to modulate SOD-2 expression. Small interfering RNA (siRNA), ribozymes, or an antisense nucleic acid that can hybridize to a nucleic acid having a sequence substantially homologous to the sequence of SEQ ID NO:1 are used in certain embodiments according to techniques for the production and use of such agents known to those of skill in the art. In yet other embodiments, an anti-SOD-2 antibody that binds to an SOD-2 peptide having an amino acid sequence substantially homologous to the sequence of SEQ ID NO:2 is used to modulate SOD-2 enzyme activity. SOD-2 enzyme activity can also be modulated using an oligonucleotide that binds to an SOD-2 peptide having an amino acid sequence substantially homologous to the sequence of SEQ ID NO:2.

IV. EXAMPLES

The present invention is further illustrated by the following examples and results, and is not to be limited in scope by the specific embodiments disclosed. Those skilled in the art will know, or be able to ascertain using no more than routine experimentation, many equivalents to the specific embodiments of the invention described herein.

Figure 1:
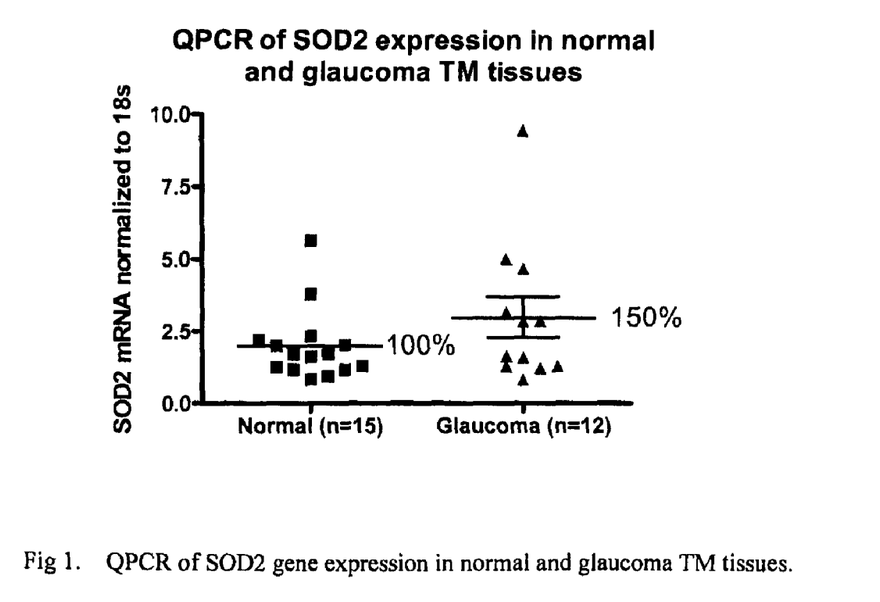
FIG. 1 is a graph of experimental results of RT-qPCR comparing SOD-2 mRNA levels in normal TM donor tissue samples to SOD-2 mRNA levels in glaucomatous TM donor tissue samples.

Embodiments of the present invention recognize in part that expression levels of SOD-2 mRNA may be elevated in glaucomatous trabecular meshwork (TM) tissue. FIG. 1 shows a graph of experimental results comparing SOD-2 mRNA levels in normal trabecular meshwork (TM) donor tissue samples to SOD-2 mRNA levels in glaucomatous TM donor tissue samples.

In the normal donor tissue sample population, only 2 of the 15 samples tested had elevated levels of SOD-2 mRNA. However, in the glaucomatous TM tissue samples, 6 of the 12 samples tested had elevated levels of SOD-2 mRNA. The average SOD-2 mRNA expression levels in the glaucomatous TM tissue samples was 150% of the average expression levels measured in normal TM tissue samples. The results of this experiment, including the results presented in FIG. 1, demonstrate that a correlation exists between elevated levels of SOD-2 mRNA in TM tissue samples and the presence of glaucoma in patients from which the tissue samples were obtained. Additional measurement of mRNA levels by Affymetrix GeneChip confirms elevated levels of SOD-2 mRNA expression in glaucomatous TM donor tissue samples.

SOD-2 mRNA levels in FIG. 1 were measured using real-time quantitative PCR (RT-qPCR). In the RT-qPCR protocol used in one embodiment of the present invention, total RNA was extracted from cultured TM cells or from RNAlater-preserved ocular tissues by using a commercial kit of RNAqueous-4 PCR (Ambion, Austin, Tex.) according to the manufacturer's instructions. RNA quality was assessed by agarose gel electrophoresis or with a 2100 Bioanalyer (Agilent). cDNA was synthesized using MultiScribe reverse transcriptase and random hexamers (PE Applied Biosystems, Foster City, Calif.). Real-time PCR was performed using the ABI Prism 7700 Sequence Detection System according to the manufacturer's instructions (Applied Biosystems, Foster City, Calif.). A typical multiplex qPCR reaction mixture consisted of 1X Taq Man Universal PCR Master Mix (Applied Biosystems, Foster City, Calif.), cDNA from 2.5 ng of total RNA, and 1 x assays-on-demand (Taqman primers/probe set) and ribosomal RNA control (18s rRNA, Applied Biosystems) in a final volume of 25 μl. Thermal cycling conditions were 50° C., for 2 minutes and 95° C. for 10 minutes, followed by 40 cycles at 95° C. for 15 seconds and 60° C. for 1minute. Relative RNA concentrations were determined by comparison to a standard curve generated by different dilutions of TM cell cDNA. SOD-2 Taqman primers/probe set (Hs00167309_ml) was purchased from Applied Biosystems. The context sequence was GAACAACAGGCCTTATTC-CACTGCT (SEQ ID NO:3).

Figure 2:
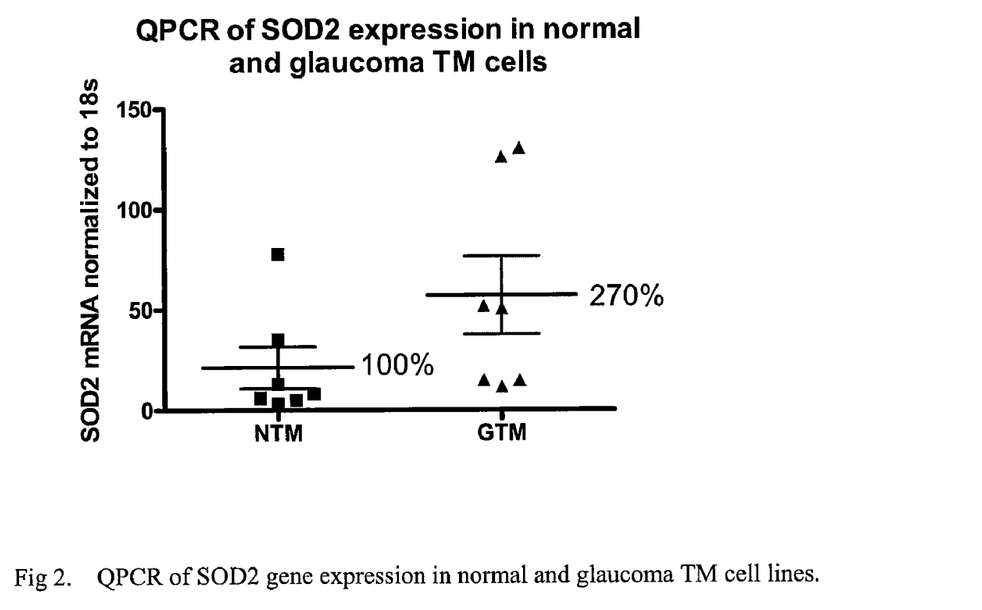
FIG. 2 is a graph of SOD-2 mRNA levels measured by RT-qPCR in control and experimental populations of TM cell lines.

FIG. 2 graphs SOD-2 mRNA levels measured in control and experimental populations of TM cell lines. In this protocol, TM cell lines were cultured using known techniques appropriate for each line. mRNA levels were measured according to the qPCR protocol described in the narrative accompanying FIG. 1.

In the 7 tested glaucomatous TM cell lines, SOD-2 mRNA levels measured by RT-qPCR were an average of 270% greater than the SOD-2 mRNA levels measured in the 7 normal TM cell lines. Information regarding the cell lines used is provided below in Table 1. FIG. 2 demonstrates that in-vitro cell cultures of glaucomatous TM cell lines express SOD-2 mRNA at much higher levels than normal TM cell line cultures.

TABLE 1

Cultured TM cells lines used for RT-qPCR of SOD2 expression

|  | # | Cell line | Age/sex of donor |
|---|---|---|---|
| Normal | 1 | TM79B, p4 | 58 M |
|  | 2 | TM57C, p3 | 65 m |
|  | 3 | TM55C, p4a | 74 F |
|  | 4 | TM12B, p4 | 77 M |
|  | 5 | TM93 | 80 M |
|  | 6 | TM94B, p5 | 82 F |
|  | 7 | TM68B, p4 | 92 F |
| Glaucoma | 1 | GTM19A, p5 | 58 F |
|  | 2 | GTM54A, p4 | 64 m |
|  | 3 | GTM62E, p4 | 74 M |
|  | 4 | GTM76D, p5 | 73 M |
|  | 5 | GTM86B, p3 | 79 M |
|  | 6 | GTM71B, p5 | 83 M |
|  | 7 | GTM52C, p4 | 90 M |

M: male; F: female

Figure 3:
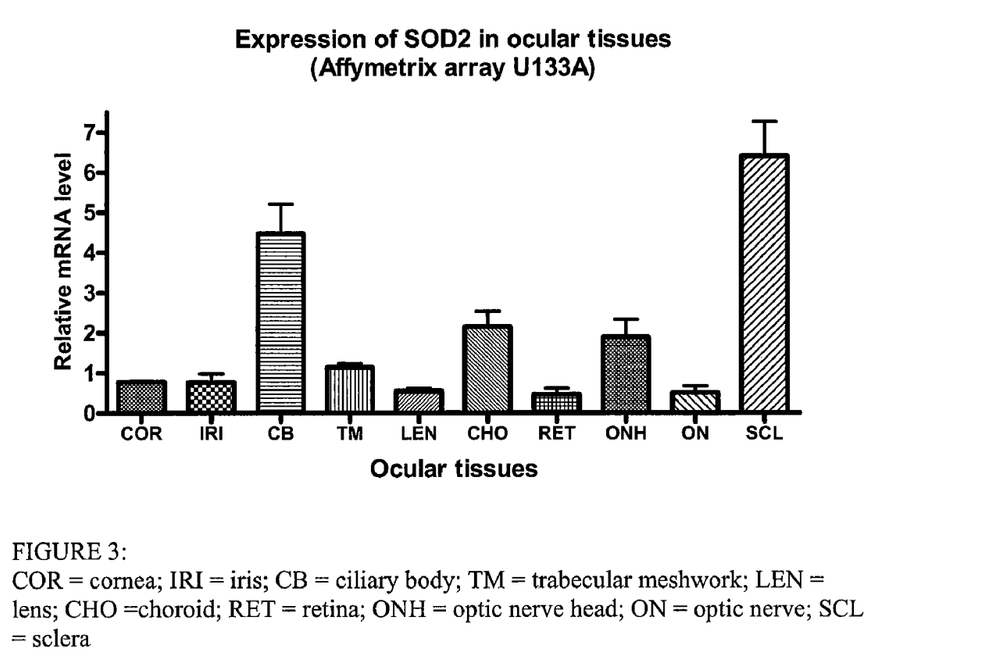
FIG. 3 is a graph showing SOD-2 mRNA levels measured by RT-qPCR in ocular tissues.

FIG. 3 is a graph showing SOD-2 mRNA levels measured in ocular tissues using an Affymetrix GeneChip protocol. In this protocol, human eyes were obtained from the Lions Eye Bank of Florida, and preserved by submersion in RNAlater solution within 6 hr post mortem. After dissection of the eye, RNA was extracted from different ocular tissues (cornea, iris, ciliary body, trabecular meshwork, RPE/choroid, optic nerve, optic nerve head, retina and sclera). Pooled RNA from 3 to 12 donors was used for analysis of gene expression by the Affymetrix GeneChips (Human Genome U133A and B). All protocols were conducted as described in the Affymetrix Genechip Expression Analysis Technical Manual (Affymetrix, Inc. Santa Clara, Calif.). Microarray data were analyzed using GeneSpring software (Agilent Technologies).

In summary, the experimental results shown in FIGS. 1-3 suggest that elevated expression of SOD-2 may be involved in glaucoma pathogenesis, and that SOD-2 mRNA is present in various ocular tissues. Accordingly, certain embodiments of the present invention diagnose glaucoma based on SOD-2 expression, screen for agents that modulate SOD-2 expression or function, and use agents that modulate SOD-2 expression to treat glaucoma.

EXAMPLE 1

In Vitro Screening Test

In an exemplary embodiment of the present invention, an in-vitro screening test is provided to determine whether test compounds modulate SOD-2 expression and possess potential uses as glaucoma therapeutics. In this embodiment, a TM cell line is treated with SAA, which causes overexpression of SOD-2. After addition of the test compound or appropriate vehicle control, the levels of SOD-2 are measured in the test and control replicates via qPCR using the protocol given in the description accompanying FIG. 1. If altered expression of SOD-2 is detected, the test compound may possess SOD-2 expression modulation properties and may have potential use as a therapeutic for glaucoma or elevated intraocular pressure.

Figure 4:
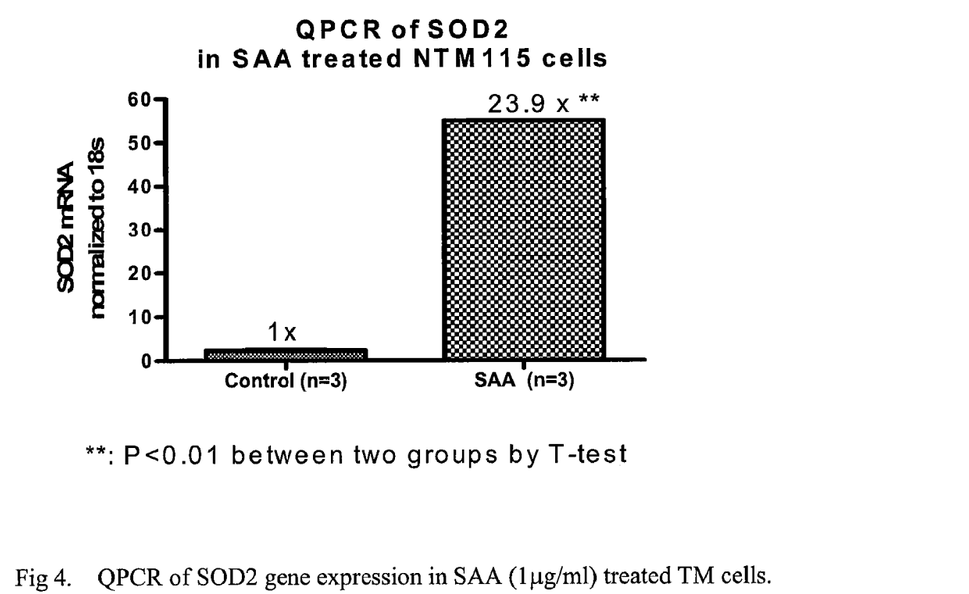
FIG. 4 is a graph of RT-qPCR results showing increased levels of SOD-2 mRNA in NTM-115 cells that are treated with SAA (serum amyloid A) compared to untreated cells.

FIG. 4 shows that cell cultures of NTM-115 cells that are treated with SAA (serum amyloid A) have increased levels of SOD-2 mRNA compared to untreated cells. In this embodiment, the TM cells of NTM-115 were cultured in 75 cm$^2$ flasks to near confluence and then treated with rhSAA (40 ug/ml) in triplicate for 24 hr. Controls were not treated. RNA samples were extracted from the cells using Trizol (Invitrogen) and purified with RNeasy MiniElute Cleanup (Qiagen). cDNA synthesized from the purified RNA was used for RT-qPCR of SOD2 expression.

EXAMPLE 2

In Vivo Evaluation of Sod-2 Upregulation on IOP

Materials and Methods

In vitro—Adv.SOD2 was constructed through a custom service (Qbiogene). TM cells (NTM469-05OS) in 12-well plates were transduced with Adv.SOD2 at a dosage of 10 and 100 pfu per cell for 24 hours in triplicate. Cells were harvested in 0.2 ml/well PBS/PI/0.5% TX-100 and the lysates were diluted 1:1000 for SOD-2 ELISA.

In vivo—Two experiments were conducted. First, a preliminary study utilized twelve Balb/c mice. The mice were divided into two groups (n=6 each group). One eye of each animal was intravitreally injected with Adv.SOD2 (treatment group) or Adv.null (vehicle group) at a dosage of 2×10$^7$ pfu/2 μl/eye. The contralateral eye of each animal was not injected. Mouse IOP was measured non-invasively in a masked manner using the Tonolab tonometer. Hyperemia of the eyes was monitored by opthalmoscope. The animals were euthanized and the eyes were enucleated at day 6 after injection. Protein was prepared from the eyes for measurement of SOD-2 by ELISA. A second, viral titer study utilized twelve Balb/c mice. The mice were intravitreally injected with Adv.SOD2 at two titers (2×10e7/eye and 9×10e7/eye, n=6 each group). IOP and hyperemia were monitored as above.

RESULTS

Figure 5:
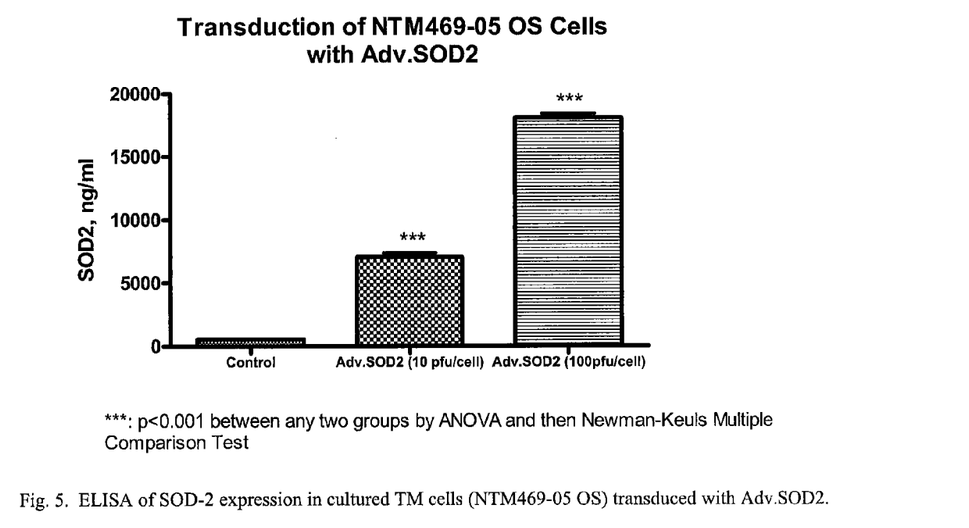
FIG. 5 shows a bar graph of ELISA-measured SOD-2 expression in cultured TM cells (NTM469-05OS) transduced with Adv. SOD2.
Figure 6:
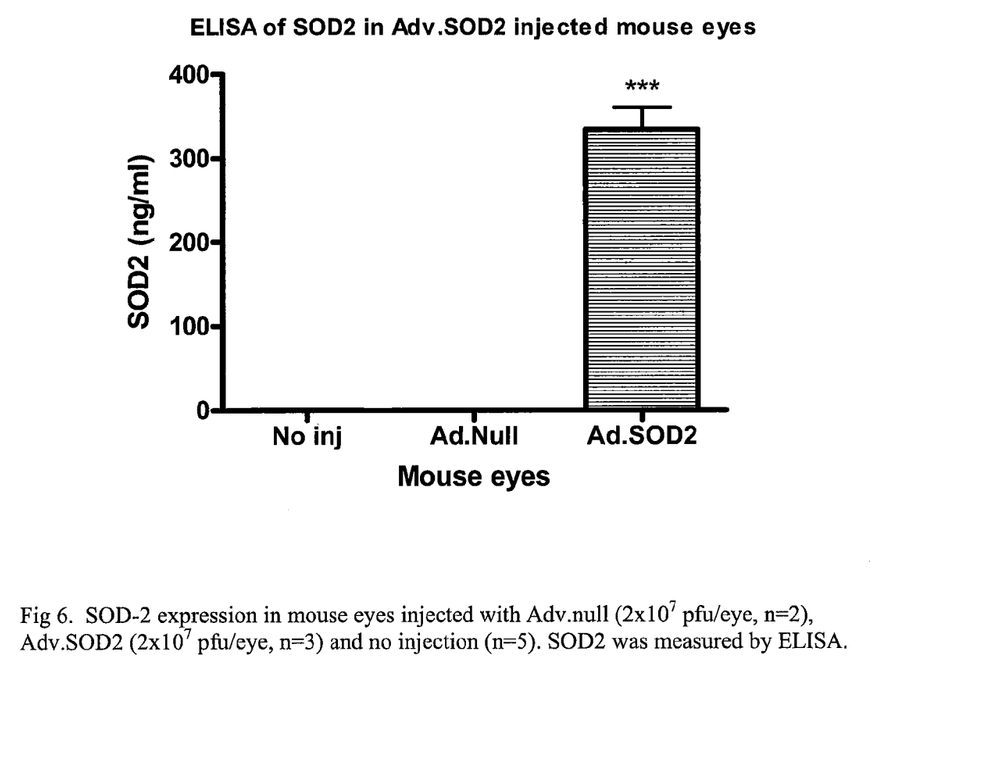
FIG. 6 shows SOD-2 expression measured by ELISA in mouse eyes.
Figure 7:
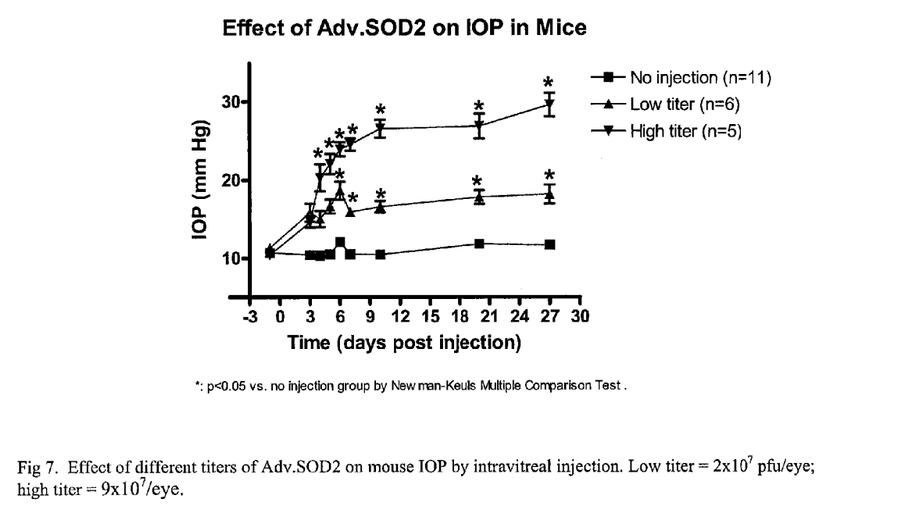
FIG. 7 shows the effect of different titers of Adv.SOD2 on mouse IOP following intravitreal injection.

FIG. 5 shows a bar graph of ELISA-measured SOD-2 expression in cultured TM cells (NTM469-05OS) transduced with Adv. SOD2. As shown in FIG. 5, a dose-dependent expression of SOD-2 was observed in Adv.SOD2 transduced TM cells. FIG. 6 shows SOD-2 expression measured by ELISA in mouse eyes. FIG. 6 shows that a significant high level of SOD-2 expression (p<0.001) was observed in Adv.SOD2 injected eyes compared to either Adv.null injected eyes or noninjected eyes. Endogenous SOD-2 was undetectable by ELISA. FIG. 7 shows the effect of different titers of Adv.SOD2 on mouse IOP following intravitreal injection. FIG. 7 shows that a dose-dependent IOP increase by injection of Adv.SOD2 was observed for up to 27 days following injection.

In summary, Adv-mediated SOD-2 was successfully expressed through either in vitro transduction of TM cells or intravitreal injection of mouse eyes. Dose-dependent IOP induction by SOD-2 was observed by IVT injection of Adv.SOD2 in mice. These results demonstrate that increased SOD-2 expression can elevate mouse IOP, providing evidence of SOD-2 linkage to glaucoma pathogenesis.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A method for assessing a risk of elevated intraocular pressure or glaucoma in a human patient comprising:
    assaying, in a human patient ocular tissue sample, the expression of a polynucleotide comprising the nucleotide sequence set forth in SEQ ID NO:1 and
    determining said risk by comparing said expression to a control level, wherein elevated expression relative to a control level correlates to increased risk.

2. The method of claim 1 wherein said assaying comprises: assaying using a probe having a nucleotide sequence complementary to that set forth in SEQ ID NO:1 or a portion thereof.

3. The method of claim 1 wherein said assaying comprises: contacting said patient sample with a microarray comprising nucleotide molecules hybridizing to said polynucleotide.

4. The method of claim 1 wherein an mRNA transcript is assayed.

5. The method of claim 4 wherein the mRNA transcript is assayed by amplification of cDNA synthesized from the mRNA transcript.

6. The method of claim 5 wherein the amplification is performed using a reverse transcription-polymerase chain reaction.

7. The method of claim 1 wherein a protein translation sequence of a nucleotide sequence comprising the sequence set forth in SEQ ID NO:1 is assayed.

8. The method of claim 7 wherein said protein translation sequence comprises the sequence of SEQ ID NO:2.

* * * * *